(12) United States Patent
Hurst

(10) Patent No.: US 6,984,259 B2
(45) Date of Patent: Jan. 10, 2006

(54) AIR DISINFECTION APPARATUS

(75) Inventor: Gordon Hurst, Crewe (GB)

(73) Assignee: UVGI Systems Limited, West Molesey (GB)

( * ) Notice: Subject to any disclaimer, the term of this patent is extended or adjusted under 35 U.S.C. 154(b) by 181 days.

(21) Appl. No.: 10/276,365

(22) PCT Filed: Apr. 17, 2001

(86) PCT No.: PCT/GB01/01711

§ 371 (c)(1),
(2), (4) Date: Jul. 30, 2003

(87) PCT Pub. No.: WO01/87362

PCT Pub. Date: Nov. 22, 2001

(65) Prior Publication Data

US 2004/0025694 A1 Feb. 12, 2004

(30) Foreign Application Priority Data

May 19, 2000 (GB) .................................. 0012040

(51) Int. Cl.
*B01D 46/00* (2006.01)
(52) U.S. Cl. ................... 95/273; 95/57; 95/63; 96/224; 96/16; 96/63; 96/68; 55/385.1; 55/385.2; 55/410; 55/357; 55/467; 55/473; 55/DIG. 39; 422/24; 422/121
(58) Field of Classification Search ................... 95/273, 95/57, 63, 69; 96/224, 16, 60, 62, 63, 64, 96/65, 66, 68, 74; 55/385.1, 385.2, 410, 55/418, 467, 473, 356, 357, DIG. 39; 422/22, 24, 121, 122; 454/187
See application file for complete search history.

(56) References Cited

U.S. PATENT DOCUMENTS

| 4,245,550 | A | | 1/1981 | Suzuki et al. | |
| 5,330,722 | A | * | 7/1994 | Pick et al. | ..................... 96/224 |
| 5,380,503 | A | * | 1/1995 | Fujii et al. | ................. 55/385.1 |
| 5,891,399 | A | * | 4/1999 | Owesen | ....................... 96/224 |
| 5,925,320 | A | * | 7/1999 | Jones | ......................... 422/121 |
| 6,053,968 | A | | 4/2000 | Miller | |
| 6,379,427 | B1 | * | 4/2002 | Siess | ........................... 96/224 |
| 6,730,141 | B2 | * | 5/2004 | Goebel et al. | ................ 96/224 |

FOREIGN PATENT DOCUMENTS

| DE | 19906113 A | 8/2000 |
| WO | WO9406482 A | 3/1994 |

* cited by examiner

*Primary Examiner*—Jason M. Greene
(74) *Attorney, Agent, or Firm*—Drinker Biddle & Reath LLP

(57) ABSTRACT

An air purification and disinfection apparatus incorporates an air inlet filter (1) spanning the intake of the apparatus, an ultraviolet light source (2) for treating the air within a chamber (14) of the apparatus, and an equalising screen (3) spanning the outlet of the apparatus. The chamber (14) is lined with a reflective sheet (11) or coating such that the ultraviolet light is reflected around the chamber (14). The air inlet filter (1) removes larger airborne particles from the airflow prior to entering the chamber (14). The light source (2) may be located in the chamber (14) or in a housing (16) which communicates with the chamber (14). With the reflective surface of the chamber (14), the intensity of the light source (2) can be maintained when dirt begins to build up on the light source (2), thereby extending the length of time that passes between each cleaning of the light source (2).

20 Claims, 2 Drawing Sheets

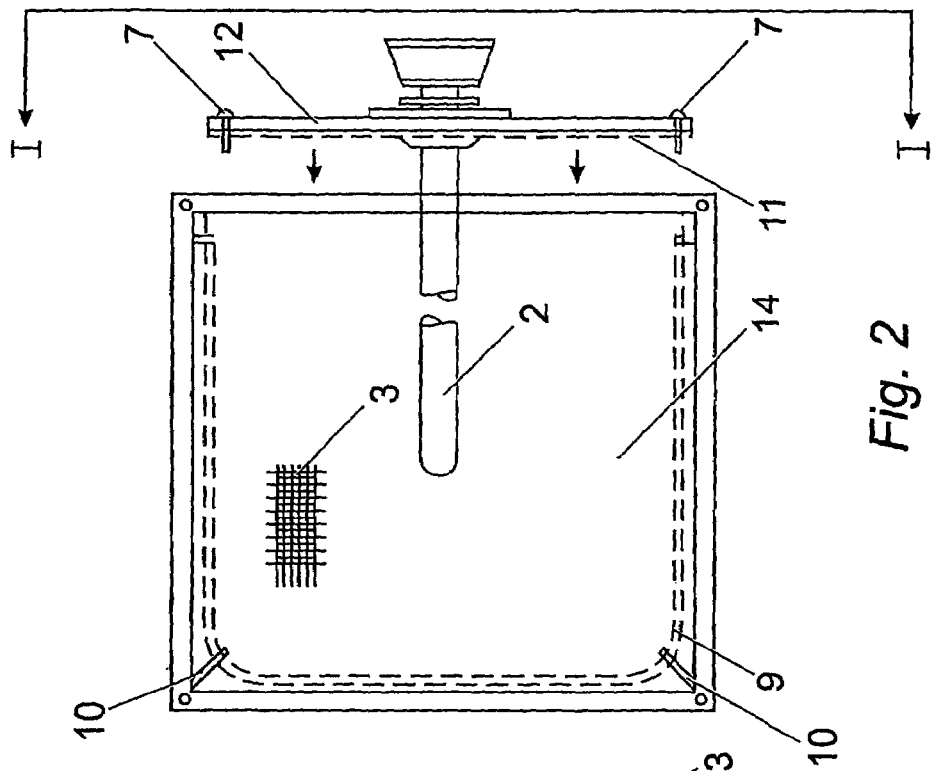
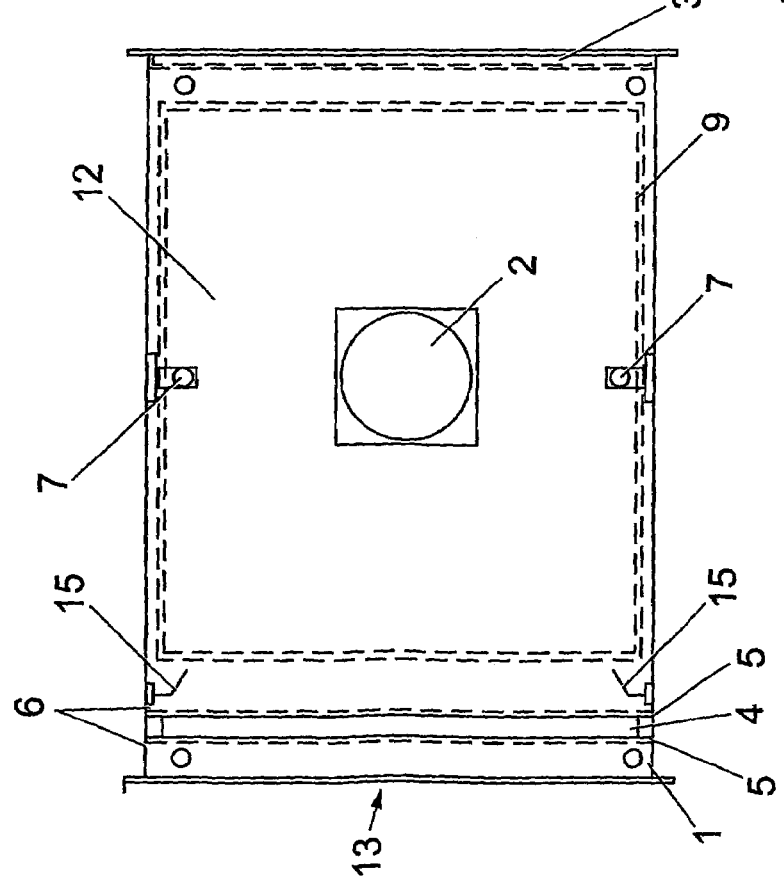
Fig. 1
Fig. 2

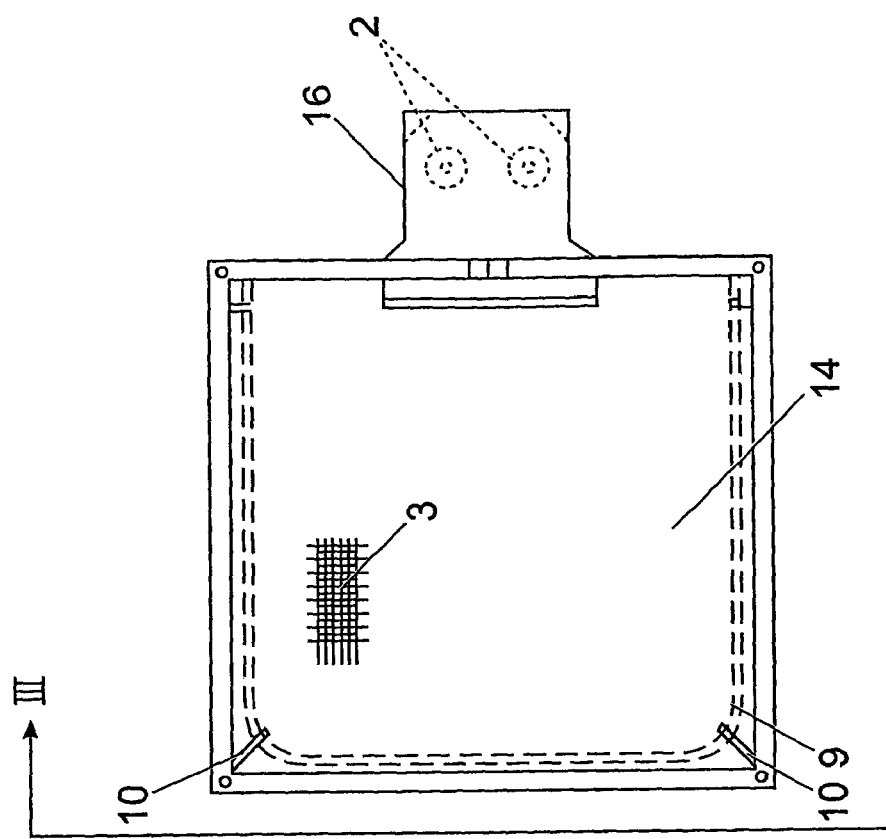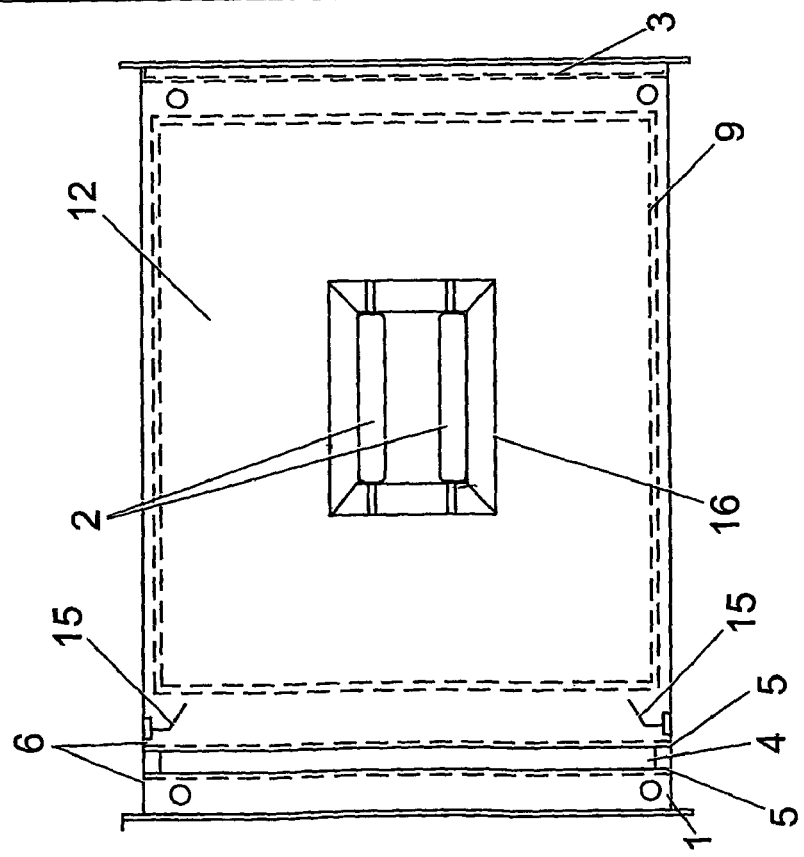

AIR DISINFECTION APPARATUS

This invention relates to apparatus for the disinfection and purification of air either in forced air systems such as air conditioning and ventilation systems, or else as a portable, stand-alone room unit.

Ultraviolet light has been used for a number of years to remove bacteria from water in the process of disinfecting and purifying the water. Ultraviolet light has also been used for the same process in relation to air in forced air systems including air conditioning and ventilation systems, although its use has been limited. The use of ultraviolet light to remove bacteria and to disinfect water has been very effective, but its use in relation to the removal of bacteria from air and the disinfection and purification of air has been less satisfactory. This is due to the reduced efficiency of the ultraviolet lamp caused by dirt particles attaching to the external surface of the lamp. Unfiltered dirt particles in a forced air system attach themselves to the ultraviolet lamp, greatly reducing its efficiency. This results in the need for regular maintenance and cleaning of the ultraviolet lamp.

An apparatus which can remove virtually all of the bacteria from the air in the forced air system will significantly reduce the respiratory problems and other health problems which are currently determined to be caused by air conditioning and ventilation systems.

It is the object of the present invention to provide a highly efficient air disinfection and purification apparatus which can be inserted in the ducting of forced air systems including air conditioning and ventilation systems. This apparatus will obtain much greater efficiency from the ultraviolet lamp and will reduce the need for maintenance and cleaning of the ultraviolet lamp. The apparatus can alternatively be portable and capable of simple positioning in a room, for example.

According to a first aspect of the present invention there is provided an air treatment apparatus comprising:
   a chamber having an input and an output;
   a filter means located adjacent said input; and
   an ultraviolet light source projecting ultraviolet light into said chamber;
   wherein said chamber has at least one light-reflective surface.

Preferably, said filter means comprises a polarised air filter.

Preferably, said apparatus further comprises an equalising screen adjacent said output.

Preferably, said at least one light-reflective inner surface comprises at least one light-reflective sheet removably inserted into said chamber.

Preferably, said at least one light-reflective sheet is an aluminium sheet. Alternatively, said at least one light-reflective inner surface comprises a surface coating applied to said at least one light-reflective surface of said chamber.

In a preferred embodiment of the first aspect of the present invention, the chamber has four inner surfaces and has a substantially rectangular cross section.

In an alternative embodiment of the first aspect of the present invention, the chamber has one inner surface and has a substantially circular cross section.

Preferably, said at least one side wall of said passage contains a removable portion. Preferably, said light source is fixedly attached to said removable portion. Preferably, said light source may be removed from said apparatus. Preferably, said light source comprises at least one ultraviolet lamp. Preferably, said at least one ultraviolet lamp emits ultraviolet light at a wavelength of between 230 nm and 290 nm.

Preferably, said light source lies in a substantially horizontal plane and is substantially perpendicular to the direction of airflow. Alternatively, said light source may lie in a substantially horizontal plane and is substantially parallel with the direction of airflow.

Preferably, said light source projects into the centre of said chamber. Preferably, said apparatus further comprises a deflector plate member located within the chamber adjacent said air filter to deflect the air flow over said light source.

Alternatively, said light source is located outwith the chamber. Preferably, said housing has at least one side wall, the inner surface of which is a light-reflective surface.

Preferably, said light-reflective surface comprises a light-reflective sheet removably attached to said inner surface. Preferably, said light-reflective sheet is an aluminium sheet. Alternatively, said light-reflective surface may be a surface coating applied to said inner surface.

In a preferred embodiment, the apparatus is located in a forced air system. In an alternative embodiment, the apparatus is portable.

According to a second aspect of the present invention, there is provided a method of treating air, comprising the steps of:
   passing air through the inlet of a chamber having at least one inner surface;
   passing the air through a filter means adjacent said inlet;
   subjecting the air to ultraviolet light within said chamber; and
   exiting the air from said chamber through an outlet,
   wherein the at least one side wall of the chamber has a light-reflective surface.

Preferably, said method uses an apparatus in accordance with the first aspect of the present invention.

Preferred embodiments of the invention will now be described by way of example only, with reference to the accompanying drawings, wherein:

FIG. 1 is a side elevation of a first embodiment of the air disinfection and purification apparatus according to the present invention;

FIG. 2, is an end elevation of the air disinfection and purification apparatus shown in FIG. 1 with the air inlet filter removed for illustrative purposes;

FIG. 3 is a side elevation of a second embodiment of the air disinfection and purification apparatus according to the present invention; and FIG. 4 is an end elevation of the air disinfection and purification apparatus shown in FIG. 3 with the equalising screen partially removed for illustrative purposes.

FIGS. 1 and 2 show a first embodiment of the air disinfection and purification apparatus incorporating an air inlet filter 1 spanning the intake of the apparatus. An ultraviolet lamp 2 is fixed centrally on a removable side panel 12 of the apparatus and an equalising screen 3 is also provided, spanning the outlet of the apparatus. The air enters the air disinfection and purification apparatus in the direction of the arrow 13, travels through a main chamber 14 housing the ultraviolet lamp 2, and discharges into the ducting of the forced air system through the equalising screen 3.

The air inlet filter 1 spans and is attached to the front of the air disinfection and purification apparatus. The air inlet filter 1 consists of a wire mesh screen 4, to which is connected a 6,000 volt DC power supply (not shown) which is fed by a 110 volt to 9 volt adapter (not shown). The wire mesh screen 4 is sandwiched between two glass fibre media pads 5 that are polarised by the high voltage present in the wire mesh screen 4. The polarised glass fibre media pads 5 themselves are sandwiched between two grounded (i.e. earthed) outside metal screens 6. An inlet air deflector plate 15 may be positioned downstream of the filter 1 to ensure that the air is deflected so as to pass over the lamp 2, although it is to be understood that this is not an essential component of the apparatus.

The inlet filter 1 is a non-ionising, low-pressure drop filter which prevents larger airborne particles from passing into the remainder of the apparatus downstream whilst not interfering significantly with the flow of air. The filter 1 may also include a non-ionising, low-pressure drop carbon insert for the removal of gases and odours. The filter 1 does not generate ozone, nor is the airflow ionised.

In this first embodiment, the ultraviolet lamp 2 is located centrally on the removable panel 12 which is attached by screw attachments 7 which are centrally placed on the top and bottom edges of the apparatus. The attachments 7 also contain micro switches (not shown) so that when the screws are removed, the switches open and the lamp 2 shuts down so that it may be removed without harming maintenance personnel.

A flexible and reflective aluminium sheet 9 covering three of the internal sides of the main chamber 14 of the apparatus is held in place by four internal guides 10, through which the aluminium sheet 9 is inserted. The internal wall of the removable panel 12 is also covered with a reflective aluminium sheet 11, so that when the removable panel 12 is attached to the main section of the apparatus, all of the internal walls of the apparatus are covered with aluminium sheet.

An equalising screen 3 spans the outlet of the air disinfection and purification apparatus. The equalising screen 3 comprises a low resistance aluminium mesh screen designed to evenly distribute the airflow as it is discharged through the outlet into the forced air system.

With the incorporation of the reflective aluminium sheet 9,11, the efficiency of the lamp 2 is greatly improved. Over time, dirt will build up on the lamp 2, reducing the effectiveness of the lamp 2 in spite of the inlet filter arrangement 1. However, the reflective sheet 9,11 compensates for this build up by reflecting the light around the chamber 14 and ensures that the ultraviolet light continues to disinfect the air during use.

In the second embodiment of the present invention, as seen in FIGS. 3 and 4, the majority of the elements described above in respect of the first embodiment are still present, and therefore will not be described again here. However, the difference between the first and second embodiments is that the ultraviolet light source 2 in the second embodiment is located in a housing 16 outwith the chamber 14. The housing 16 is fixed, by bolts, screws or the like to a side of the air duct. The housing 16 can either be manufactured from a reflective material such as Aluminium, for example, or else reflective sheet such as that used in the duct may be inserted into the housing 16. The housing 16 may also be fitted with a prevention screen (not shown) to prevent ozone from entering the chamber 14.

Therefore, in the second embodiment, the ultraviolet light emitted from the light source 2 may be directed into the chamber 14 by the reflective material without the light source 2 having to be positioned in the chamber 14. Thus, there will be no build up of deposits on the light source 2 during operation, and the light source 2 will therefore not require cleaning.

The preferred ultraviolet light source in both of the aforementioned embodiments is one or more ultraviolet arc-tubes. The arc-tubes can either be controlled from a integrated control panel (e.g. first embodiment) or a remote control panel (e.g. second embodiment). The action of the ultraviolet light, preferably at wavelengths from 230 nm to 290 nm, causes microbial and viral disruption of the passing airflow.

As a result of the present invention, the air in forced air systems such as air conditioning and ventilation systems can be disinfected and purified by removing bacteria with minimal loss of airflow and a greatly reduced need for maintenance and cleaning.

For the application of the present invention in forced air systems, a number of advantages are gained over existing systems. One of the prime advantages is that the reflective nature of the aluminium sheet 9, 11 contained in the main chamber 14 of the apparatus increases the efficiency of the apparatus by ensuring that the strength of the ultraviolet light is evenly distributed throughout the chamber 14. With respect to the first embodiment, the even distribution of the ultraviolet light due to the high reflectivity of the aluminium sheet 9, 11 compensates for the reduced output of ultraviolet light from the ultraviolet lamp 2 as dirt particles attach to the external surface of the ultraviolet lamp 2 over time.

The air filter 1 greatly reduces the dirt particles entering the main section of the apparatus and thereby will also reduce the loss of efficiency of the ultra violet lamp 2.

Another advantage of the present invention is that whilst the air disinfection and purification apparatus can be installed during the construction of new forced air systems, including air conditioning and ventilation systems, it can also be fitted into existing forced air systems.

A further advantage is that the need to clean and replace the ultraviolet lamp 2 is either greatly reduced or obviated altogether. It is expected that the first embodiment of the present invention will efficiently remove bacteria from the airflow travelling through the forced air system for six months without the need for cleaning. At present, existing ultraviolet systems require the lamps to be cleaned at least once every two months or so. It is anticipated that the second embodiment of the present invention will not require any cleaning at all.

The filters used in the air inlet filter are comprised of low cost dispensable media and can be removed and replaced at three monthly intervals. As a result the cleaning and maintenance of the air disinfection and purification apparatus will only require to be carried out quarterly, thereby reducing the cleaning and maintenance costs substantially.

It is anticipated that the air disinfection apparatus has a number of other applications other than its use in air conditioning and ventilation systems in buildings. Similar systems may also be incorporated in cars, buses, sea-faring vessels and aeroplanes and any other manufacturing application which would benefit from the disinfection and purification of air circulating in a forced air system.

Modifications and improvements can be incorporated without departing from the scope of the invention.

For example, although the aforementioned embodiments describe the invention when located in a forced air system, it is also possible to produce the apparatus as a portable unit. In this way, the unit can be placed anywhere in a room and operate in the same manner as described above.

Furthermore, although it is anticipated that the reflective sheet covering the internal walls of the chamber and housing is made of aluminium sheet, the scope of the invention is not limited to the use of aluminium sheet. Any other material whether metallic or non-metallic that is suitably pliable and reflective may be used in place of aluminium sheet. Furthermore, the reflective sheet may be replaced altogether with a suitable reflective coating applied to the relevant surfaces.

Another modification could be to reposition the light source of the first embodiment such that it is substantially parallel to the airflow rather than transversely positioned. It has been shown that having the light source oriented in such a way may further improve the efficiency of the apparatus.

What is claimed is:

1. An air treatment apparatus comprising:
   a treatment chamber having an input and an output and at least one light-reflective inner surface;
   a filter means located adjacent the input; and
   an ultraviolet light source located downstream of the filter and projecting ultraviolet light into the treatment chamber,
   wherein the light source is located outwith the treatment chamber.

2. The apparatus of claim 1, wherein the light source is located within a housing outwith the treatment chamber, the housing having at least one side wall and an aperture adapted to permit projection of the ultraviolet light into the treatment chamber, the inner surface of the at least one side wall being a light-reflective surface.

3. The apparatus of claim 2, wherein the aperture is provided with an ozone prevention screen.

4. The apparatus of claim 2, wherein the light-reflective surface of the housing comprises a light-reflective sheet removably attached to the inner surface.

5. The apparatus of claim 4, wherein the light-reflective sheet is an Aluminium sheet.

6. The apparatus of claim 2, wherein the light-reflective surface of the housing is a surface coating applied to the inner surface.

7. The apparatus of claim 1, wherein the filter means comprises a polarised air filter.

8. The apparatus of claim 1, wherein the apparatus further comprises an equalising screen adjacent said output.

9. The apparatus of claim 1, wherein the at least one light-reflective inner surface of the treatment chamber comprises at least one light-reflective sheet removably inserted into the treatment chamber.

10. The apparatus of claim 9, wherein the at least one light-reflective sheet is an Aluminium sheet.

11. The apparatus of claim 1, wherein the at least one light-reflective inner surface of the treatment chamber comprises a surface coating applied to the at least one inner surface of the treatment chamber.

12. The apparatus of claim 1, wherein the treatment chamber has four inner surfaces and a substantially rectangular cross section.

13. The apparatus of claim 1, wherein the treatment chamber has one inner surface and has a substantially circular cross section.

14. The apparatus of claim 1, wherein the light source comprises at least one ultraviolet lamp.

15. The apparatus of claim 14, wherein the at least one ultraviolet lamp emits ultraviolet light at a wavelength of between 230 nm and 290 nm.

16. The apparatus of claim 1, wherein the light source may be removed from the apparatus.

17. The apparatus of claim 1, wherein the apparatus is located in a forced air system.

18. The apparatus of claim 1, wherein the apparatus is portable.

19. A method of treating air comprising the steps of:
    passing air through the inlet of a treatment chamber having at least one light-reflective inner surface;
    passing the air through a filter means adjacent said inlet;
    subjecting the air to ultraviolet light within said treatment chamber; and
    exiting the air from said treatment chamber through an outlet,
    wherein the light source is located outwith the treatment chamber.

20. A method of treating air comprising the steps of:
    passing air through a treatment chamber having an input and an output and at least one light-reflective inner surface;
    passing the air through a filter means located adjacent the input;
    providing an ultraviolet light source outwith the treatment chamber and located downstream of the filter;
    directing ultraviolet light from the ultraviolet light source into the treatment chamber;
    subjecting the air to ultraviolet light within the treatment chamber; and
    exiting the air from the treatment chamber through the output.

* * * * *